(12) United States Patent
Phillips et al.

(10) Patent No.: US 12,048,515 B2
(45) Date of Patent: Jul. 30, 2024

(54) ARTERIAL COMPLIANCE DETECTOR

(71) Applicant: Epic Neuro, Inc., Fountain Valley, CA (US)

(72) Inventors: James William Phillips, Fountain Valley, CA (US); Robert Abrams, Los Gatos, CA (US)

(73) Assignee: Epic Neuro, Inc., Fountain Valley, CA (US)

( * ) Notice: Subject to any disclaimer, the term of this patent is extended or adjusted under 35 U.S.C. 154(b) by 0 days.

(21) Appl. No.: 16/784,156

(22) Filed: Feb. 6, 2020

(65) Prior Publication Data

US 2021/0401302 A1 Dec. 30, 2021

Related U.S. Application Data

(60) Provisional application No. 62/803,258, filed on Feb. 8, 2019.

(51) Int. Cl.
*A61B 5/02* (2006.01)
*A61B 5/00* (2006.01)
*A61B 5/0215* (2006.01)

(52) U.S. Cl.
CPC ........ *A61B 5/02014* (2013.01); *A61B 5/0215* (2013.01); *A61B 5/6862* (2013.01)

(58) Field of Classification Search
CPC .................. A61B 5/02007; A61B 5/02014
See application file for complete search history.

(56) References Cited

U.S. PATENT DOCUMENTS

| 8,690,785 B2* | 4/2014 | Lading | A61B 5/021 600/485 |
| 2004/0133092 A1* | 7/2004 | Kain | A61B 5/0031 600/377 |
| 2005/0065592 A1* | 3/2005 | Holzer | A61F 2/88 623/1.36 |
| 2019/0076033 A1* | 3/2019 | Sweeney | A61B 5/6882 |

OTHER PUBLICATIONS

Zhu et al.; Ultrastretchable fibers with metallic conductivity using a liquid metal alloy core; Advamced Functional Materials; 23(18); pp. 2308-2314; May 2013.

* cited by examiner

*Primary Examiner* — Jacqueline Cheng
*Assistant Examiner* — Tho Q Tran
(74) *Attorney, Agent, or Firm* — Shay Glenn LLP

(57) ABSTRACT

A device which provides a measure of the compliance of a vessel wall based on a change in pressure, which causes the vessel to distend. The device comprises a coil and capacitor, forming a tank circuit. The coil is expandable and positioned along a portion of the vessel so that when the portion of the vessel expands or contracts, the coil will also expand or contract, changing the area in side the coil. This change in area alters the coil inductance, and therefore the resonant frequency of the tank circuit, which can be detected externally.

15 Claims, 6 Drawing Sheets

ARTERIAL COMPLIANCE DETECTOR

BACKGROUND

Arterial compliance is a measure of the amount of stretching or widening that occurs in an artery during a heartbeat. Arterial distension allows for a buffering of blood pumped from the heart throughout the body. This is generally referred to as the Windkessel effect. Because arteries distend when blood pressure rises during systole and recoil when blood pressure falls during diastole, a damping occurs in the fluctuation in blood pressure over the cardiac cycle, and assists in maintaining organ perfusion during diastole after cardiac ejection.

By measuring arterial compliance during the cardiac cycle, information may be obtained regarding the stiffness of the arterial wall and the change in blood pressure between systole and diastole. It can also give an estimate of blood perfusion into a region of the artery. For example, if the measured arterial compliance decreases over a period of time, it could indicate potential heart failure or arteriosclerosis.

Currently, arterial compliance is estimated using indirect means, such as Pulse Wave Velocity (PWV) or Doppler-Echocardiography. PWV uses two pressure catheters and evaluates the time required for the pressure wave to travel from the upstream pressure catheter to the downstream pressure catheter. This provides an overall arterial compliance estimate, but does not provide a compliance estimate of a specific location. Doppler-Echocardiography uses doppler ultrasonography to record blood velocity and annulus diameter simultaneously, which gives an indication of compliance in the tested region. This method is mainly used for larger vessels, such as the aorta.

An aneurysm is a bulging, weakened area in the arterial wall. This results in an abnormal widening, ballooning, or bleb. The wall of an aneurysm is thin and weak because of an abnormal loss or absence of the muscular layer of the artery wall. Aneurysms are at risk for rupturing, potentially causing a subarachnoid hemorrhage, resulting in significant injury or death of the person. Cerebral aneurysms can be especially dangerous, due to the potential for permanent brain damage. The risk of cerebral aneurysm rupture is about 1 percent per year, but may vary depending on the size and location of the aneurysm.

The most common type of cerebral aneurysm is the saccular aneurysm, occurring in 90 percent of cerebral aneurysms. These aneurysms resemble a "berry" with a narrow stem. Due to the narrow weaker wall of an aneurysm, the compliance of the aneurysm is significantly higher than for the vessel which feeds the aneurysm. By measuring the compliance of the aneurysm wall, an estimate can be made of the chance of a rupture.

One of the most commonly used methods of treating an aneurysm is through endovascular coiling, in which the aneurysm is filled with a soft coil of wire that closes off the sac and reduces the risk of bleeding. Multiple coils are packed inside the dome to block normal blood flow from entering. Over time, a clot forms inside the aneurysm, effectively removing the risk of a rupture.

In approximately 5-10% of cases, the coil does not completely fill the aneurysm, resulting in a continued weak spot and potential rupture, necessitating recoiling. Recurrence happens if the coils do not completely block off the aneurysm or if the coils become compacted within the aneurysm. patients with coiled aneurysms generally return after 6, 12, and 24 months for a diagnostic angiogram to monitor for a residual or recurring aneurysm.

A diagnostic angiogram requires a catheter inserted into an artery in the leg or arm. Using x-ray guidance, the catheter is navigated to the aneurysm site and a contrast material is injected, with x-ray images captured. The procedure is invasive, time consuming, and painful to the patient. Clearly, a demand exists for a method or device to determine arterial compliance without the use of a diagnostic angiogram.

SUMMARY

In broad terms, the present invention provides a measure of the compliance of a vessel wall based on a change in pressure, which causes the vessel to distend. The device for measuring the compliance of a vessel wall comprises a coil having a number of turns and a capacitor, wherein the coil and the capacitor are connected in series forming a tank circuit, and the coil is expandable and positioned along a portion of the vessel so that when the portion of the vessel expands or contracts, the coil will also expand or contract, causing a change in the area inside the coil. In one aspect of the device, the coil is positioned so that it encircles the vessel.

In one aspect of the device, the vessel is an artery of a mammal. Assuming the vessel wall remains structurally unchanged, then a change in diameter can give an indication of the change in pressure causing the distension of the vessel. By implanting multiple devices in a vessel, it is possible to get an indication of change in pressure distribution throughout the vessel. For example, if two devices are implanted at two locations in an artery, then a difference in pressure between the upstream and downstream locations in the vessel may indicate an occlusion to proper blood flow.

In one aspect of the device, the coil is attached to a stent so that when the stent expands or contracts, the coil will also expand or contract with the stent. If a device is positioned at each end of the stent, then by measuring compliance, the pressure differential along the stent may be estimated, which may give an indication that in-stent restenosis or some other occlusion is occurring in the stent.

In one aspect of the device, the vessel is an aneurysm. An aneurysm has significant compliance, due to thinning of the wall of the aneurysm. By measuring the compliance of the aneurysm wall, it may be possible to determine the potential for rupture of the aneurysm. In addition, if a coiling procedure is performed, the device may give an estimate of blood flow into the aneurysm during the cardiac cycle, which may indicate that a recoiling is required.

In one aspect of the device, the capacitor has a variable capacitance based on a characteristic of an environment around the capacitor. In one aspect, the variable capacitance is based on pressure. By measuring pressure as well as compliance, it may be possible to determine a possible structural change in the vessel wall. For example, if the same change in pressure results in significantly more distension of the vessel wall, then the wall itself is becoming more compliant or flexible, possibly due to thinning. In addition, measuring of pressure along with vessel compliance may provide a redundancy to make the pressure measurement more accurate.

In one aspect of the device, the capacitor is created using two electrodes exposed to a material inside the vessel, wherein the capacitance is a result of electrode-material interface capacitance of each electrode. The short-term change in resonant frequency of the tank circuit due to coil expansion and contraction allow for a measure of the compliance of the vessel and pressure inside the vessel, and the gradual change in resonant frequency due to a change in the electrode-material interface indicates a change in the characteristics of the material inside the vessel.

DETAILED DESCRIPTION

Figure 1:
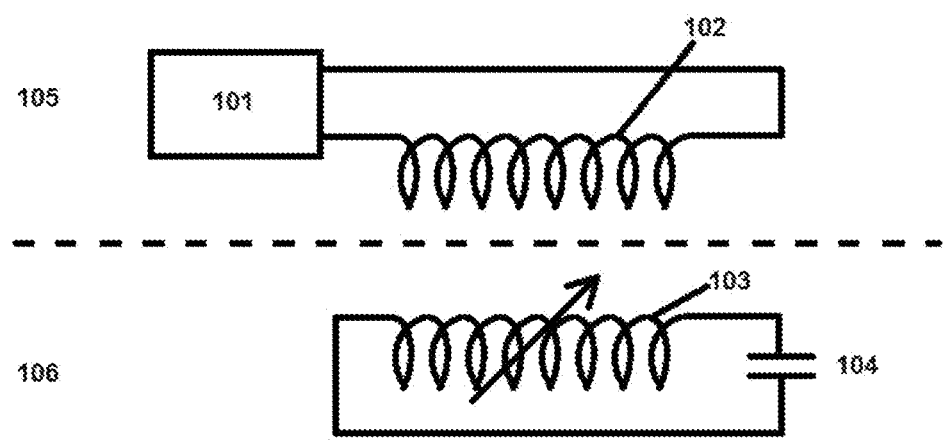
FIG. 1 is a system level schematic in which wireless transmission of the vessel compliance is accomplished with one embodiment of the device.

While certain embodiments have been provided and described herein, it will be readily apparent to those skilled in the art that such embodiments are provided by way of example only. It should be understood that various alternatives to the embodiments described herein may be employed, and are part of the invention described herein.

Provided herein is a device whereby compliance of a vessel is determined. In one aspect, the vessel is be an artery in a person. During the cardiac cycle, blood pressure raises significantly during systole and lessens during diastole. For example, in adults, blood pressure during systole may be 130 mmHg, and during diastole it may lower to 90 mmHg. The increase in blood pressure causes the artery to distend, causing the diameter and the cross-sectional area of the artery to increase. When blood pressure is reduced, the artery will relax and return toward its original size, with a lower cross-sectional area of the artery.

In one aspect of the device, it comprises a coil, which is expandable, and the coil is positioned along the artery wall, so that when the artery expands, the coil will expand as well. When the coil expands, the area within the coil increases. Therefore, the area within the coil will increase when the artery distends due to increased pressure, and will decrease when the artery returns to its original size due to decreased pressure.

The coil's expandability may be accomplished by selecting a material for the coil that will stretch, but is still conductive. For example, ultra-stretchable fibers (Zhu, et al., 2012) have been developed that are stretchable hollow fibers containing a liquid metal alloy, eutectic gallium indium. In another example, the coil includes a series of bends, forming a corrugated circular shape. In this way, when the coil expands, the angle of the bends becomes greater and the corrugated shape flattens out, allowing the coil to increase in size. When the coil decreases in size, the coil reverts back to its original corrugated shape. Other techniques may exist to those skilled in the art in order to make the coil expandable.

In order to measure the compliance of a vessel, it is necessary to position the coil in such a way that when the vessel distends, the area inside the coil increases. In one example, the coil encircles the vessel, either on the inside or outside of the vessel wall. During systole, the artery will distend, causing an increase in the area inside the coil, and during diastole, the artery will relax, causing a decrease in the area of the inside of the coil.

Coil inductance L can be given by the following equation:

$$L = N^2 \mu_0 \mu_r \left(\frac{D}{2}\right)\left(\ln\left(\frac{8D}{d}\right) - 2\right)$$

where N is the number of turns in the coil, μ0 is the permeability of free space, μr is the relative permeability of the substance within the loop, D is the diameter of the loop, and d is the diameter of the wire. In one aspect of the device, a 16-turn coil using 40 gauge wire (diameter 0.08 mm) with a 3 mm loop diameter, and assuming blood is flowing through the coil with a relative permeability of approximately 1.0, the coil inductance would be 1.79 μH. If the coil diameter increased to 3.5 mm, the inductance would change to 2.17 μH, a 21% increase in inductance.

The device described herein provides wireless telemetric sensing of the vessel wall. The LC tank circuit couples to a separate, external transmitting coil via mutual inductance. The change in compliance during a cardiac cycle can be seen in a characteristic change in impedance and phase. The resonant frequency ω0 of the LC tank circuit can be found using the following equation:

$$\omega_0 = \frac{1}{\sqrt{LC}}$$

where L is the variable inductance and C is the series capacitor. if, as in the previous example, the inductance increases by 21%, the resonant frequency will decrease by 9.1%. Impedance interrogation can be performed using an impedance analyzer or other device connected to an interrogator coil that is placed as close as possible to and in line with the device coil. A time varying current may be passed through the interrogator coil, which generates a time-varying magnetic flux that links the loop in the device coil. The determination of the resonant frequency in the device coil may be then found by evaluating the detected impedance of the coupled coil system. Such calculations are well known to those skilled in the art.

In the examples described above, the vessel is an artery in a body. However, the vessel does not need to be an artery.

For example, the vessel could be a catheter or other conduit or container, which distends under pressure.

In another example, compliance of the wall of an aneurysm may be found by positioning an expandable coil so that when the aneurysm expands and contracts during a cardiac cycle, the coil area will change and the resulting inductance change can be detected through a change in resonant frequency. Due to the thinning of the vessel wall of an aneurysm, its compliance may be significantly greater than the compliance of an arterial wall. Multiple devices can be positioned in an aneurysm, each detecting distension of a different part of the aneurysm. In this way, it is possible to determine the amount of blood flow into and out of the aneurysm, which gives an indication of how likely the aneurysm is to grow or burst. The devices may be positioned in the aneurysm before a coiling procedure is performed, in order to test to see how well the coiling process did at isolating the aneurysm.

Coiling is a common procedure to treat an aneurysm, involving a flexible wire to be fed into the aneurysm, effectively filling the space and providing structural support, with clotting and fibrosis closing off the aneurysm to blood flow. However, in some cases, the coil does not close off the aneurysm completely, allowing blood to continue to flow into the aneurysm. When this happens, the portion of the aneurysm wall where blood flows will continue to distend, with a risk of rupturing or causing a secondary aneurysm to develop. In one example, the device coil is positioned near the neck of the aneurysm before the coiling process begins. The device can then detect any distension of the aneurysm due to residual blood flow from incomplete coiling.

Stents are often implanted in an artery in order to provide structural support and to allow blood flow through that portion of the vessel. When the artery expands due to change in pressure during a cardiac cycle, the stent will expand as well. Therefore, in one aspect of the device, the coil is attached to a stent so that the device can detect compliance of the artery when the stent changes shape. For example, a device coil may be attached to the end of the stent so that the coil encircles the stent. The coil is expandable, and may be folded in such a way that it can be implanted with the stent using catheter implantation processes known to those skilled in the art. multiple devices may be implanted along the stent in order to measure compliance at multiple locations, or as a redundancy.

If multiple devices are implanted in a vessel, it may be necessary to distinguish between them. This may be done by altering the capacitance of each device, so that they have a unique resonant frequency. Also, each device may have a different number of turns in the coil, which changes the inductance and allows an external impedance analyzer and interrogation coil to differentiate between devices.

FIG. 1 shows a system level schematic in which wireless transmission of the vessel compliance is accomplished with one embodiment of the device. An expandable coil with a number of turns 103 is positioned in a vessel. The capacitor 104 is electrically connected in series with the coil, forming a tank circuit 106. The variable inductance of the coil allows the resonant frequency of the circuit to vary based on the area inside the coil.

In addition to passive telemetric communication of the vessel compliance, power is transmitted wirelessly to the tank circuit from a separate, external system 105 comprising an interrogation coil 102. In this embodiment, the tank circuit wirelessly loads down the interrogation coil such that a change in vessel size can be detected by a shift in the resonant frequency, where the interrogation coil shows a characteristic dip in impedance. The frequency shift or impedance change can be detected through a spectrum analyzer 101 or other impedance measuring device known to those skilled in the art. The spectrum analyzer may also include a signal generator. In the passive telemetry embodiment of FIG. 1, both the interrogation coil and spectrum analyzer and power source reside outside the body or other structure where the vessel is located. It is possible, however, for active telemetric methods to be used that benefit from the change in inductance based on vessel size. This may involve an implanted chip either integrated with, or discrete from the tank circuit described.

Figure 2A:
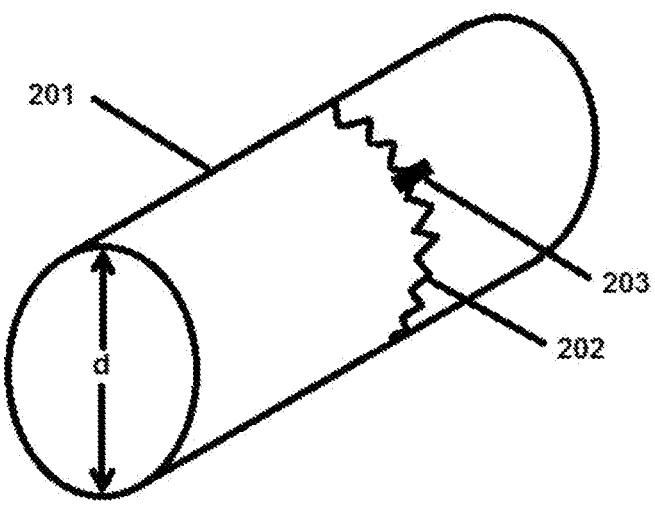
FIG. 2A shows an exemplary device in which the coil is positioned so that it encircles the interior of an artery with the vessel contracted.
Figure 2B:
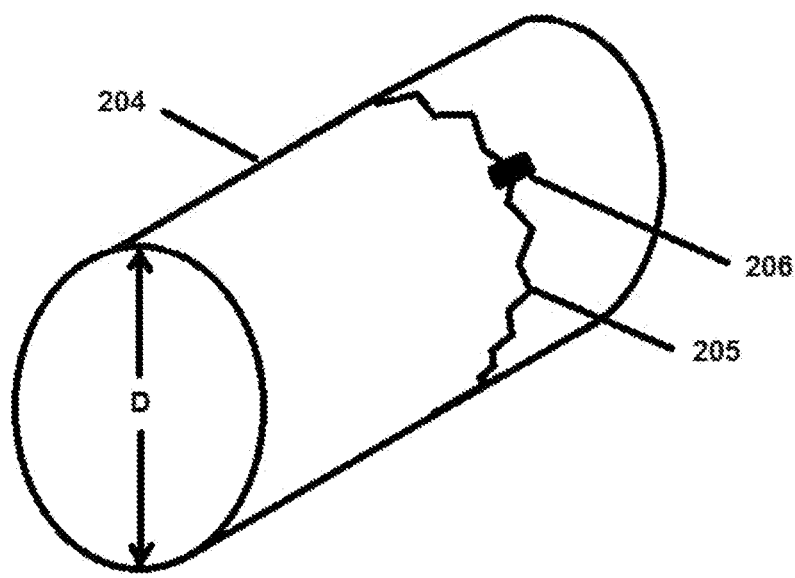
FIG. 2B shows an exemplary device in which the coil is positioned so that it encircles the interior of an artery with the vessel expanded.

FIG. 2A shows an exemplary device in which the coil 202 is positioned so that it encircles the interior of an artery 201. The artery is not distended and has a small diameter d, since the pressure is low. Therefore, the coil includes several corrugated bends, which causes the interior area of the coil to be small. A capacitor 203 is attached in series with the coil to form a tank circuit. FIG. 2B shows the same device, with the artery 204 distended, having a larger diameter D>d. This results in the coil 205 being less corrugated in shape, taking up a larger area. The capacitor 206 is connected in series with the coil to form the tank circuit. In this case, the larger coil diameter will result in an increased inductance, lowering the resonant frequency of the tank circuit.

Figure 3:
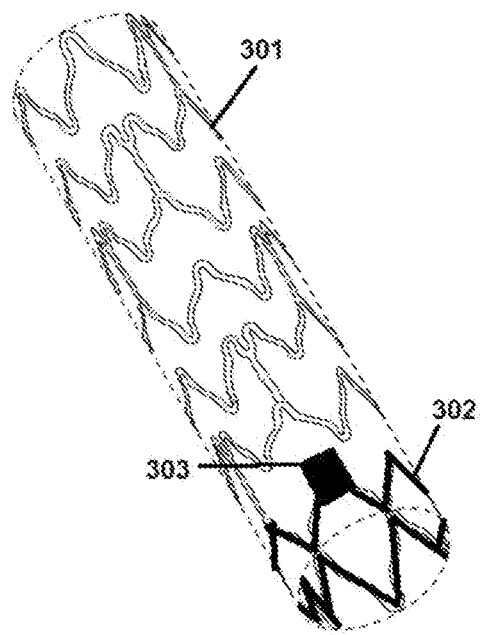
FIG. 3 is an exemplary device in which the coil is attached to a portion of a stent, such that the coil expands when the stent expands.

Holding the device in place in an artery may be challenging, since blood is flowing through the center of the coil and the artery is continually expanding and retracting. Therefore, the coil may be attached to a structure that is within the artery. FIG. 3 shows an exemplary device in which the coil 302 is attached to a portion of a stent 301. The capacitor 303 is attached in series with the coil 302. In this way, when the stent changes in diameter due to a change in artery size, the coil will change as well.

Figure 4:
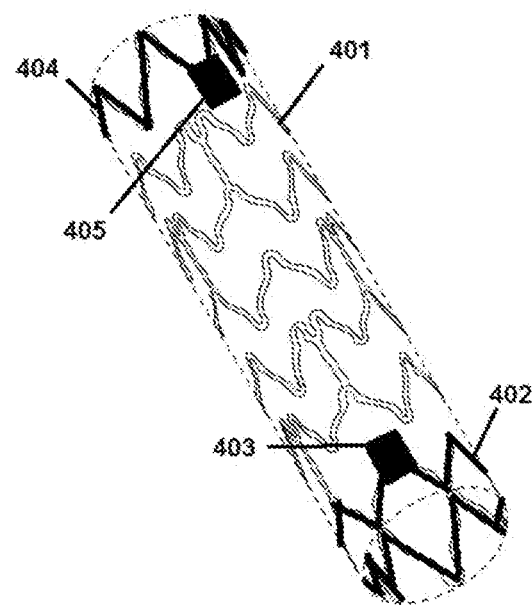
FIG. 4 is an exemplary usage of the device in which two devices are attached to each end of a stent, such that expansion and contraction of the stent is determined along the length of the stent.

It may be advantageous to detect arterial compliance at multiple locations in the artery, either to provide a comparison to calculate flow rate or some other metric, or as a redundancy. For example, if the device is part of a stent, then multiple devices may be attached to the stent. FIG. 4 shows two exemplary devices attached to each end of a stent 401. The two coils 402, 404 are attached to the stent, and the capacitors 403, 405 are attached in series with the coils. In order to differentiate between the two coils, the capacitance or number of turns in the coil can be different between the two devices, so that they each have a distinct resonant frequency for the same internal area. Since the compliance, or distension, of the artery is dependent on the pressure inside the artery, by having multiple devices, it is possible to measure the difference in pressure between two points in the artery. This may be useful to determine, for example, that a potential restriction in flow exists between the two devices. If the devices are at opposite ends of a stent, as shown in FIG. 4, then it may be possible to detect in-stent restenosis developing. By getting an idea of flow rate during the cardiac cycle, it may also be possible to determine whether heart failure is occurring in the person.

Figure 5:
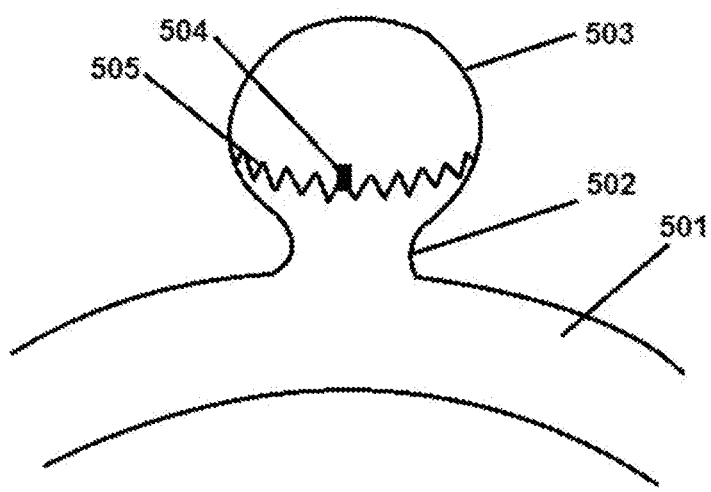
FIG. 5 is an exemplary device positioned in an aneurysm, where when the aneurysm expands and contracts due to the cardiac cycle, the device coil will expand and contract accordingly.

One example location where arterial compliance is valuable to measure is the wall of an aneurysm, due to its increased likelihood to rupture. The wall of an aneurysm is thin, which increases its compliance, causing the aneurysm to distend significantly when pressure is increased during a cardiac cycle. In one aspect of the device, it Is positioned so that the stretchable coil is along the wall of the aneurysm, allowing the inductance to change each time the aneurysm expands or retracts. FIG. 5 shows an exemplary device positioned in an aneurysm 503. The device coil 505 folds in on itself in an accordion fashion to allow proper placement in the aneurysm and to be fed through the artery 501 and the neck of the aneurysm 502. Preferably, the coil self-expands to fill the aneurysm space, and will expand more when the aneurysm distends due to increased pressure. The capacitor 504 is as small a size as possible, so as to fit within a catheter and not interfere with the coil expansion or retraction. A surface mount capacitor size 0201 with dimensions 0.6×0.3 mm would work well. However, if a smaller capacitor is required, the 008004 size with dimensions 0.25×0.125 mm would definitely fit.

Figure 6:
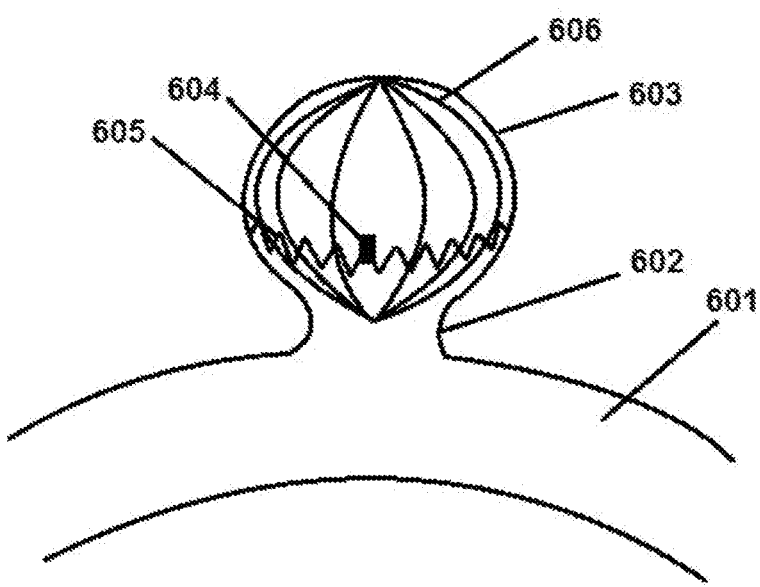
FIG. 6 is an exemplary device implanted in an aneurysm where the expandable coil is affixed to a hollow ribbed ball-shaped structure, which ensures that the coil is held in place, and also provides additional support to the aneurysm for a potential coiling procedure.

To properly position the device in an aneurysm, it may be necessary to mount it to a structure that is implanted with the device. FIG. 6 shows an exemplary device implanted inside an aneurysm 603 where the expandable coil 605 is affixed to a hollow ribbed ball-shaped structure 606. The ribbed structure fills the space and can also act as structural support for a coiling procedure. The device should preferably be mounted to the ribbed structure using a spring or other connector that will allow the coil to expand or contract without the ribs of the structure needing to change shape. The hollow ribbed structure and device can be compressed so as to fit inside a catheter to allow proper placement via a catheter through the artery 601 and neck of the aneurysm 602. The capacitor 604 must be of small enough size to fit in the catheter as well.

Figure 7:
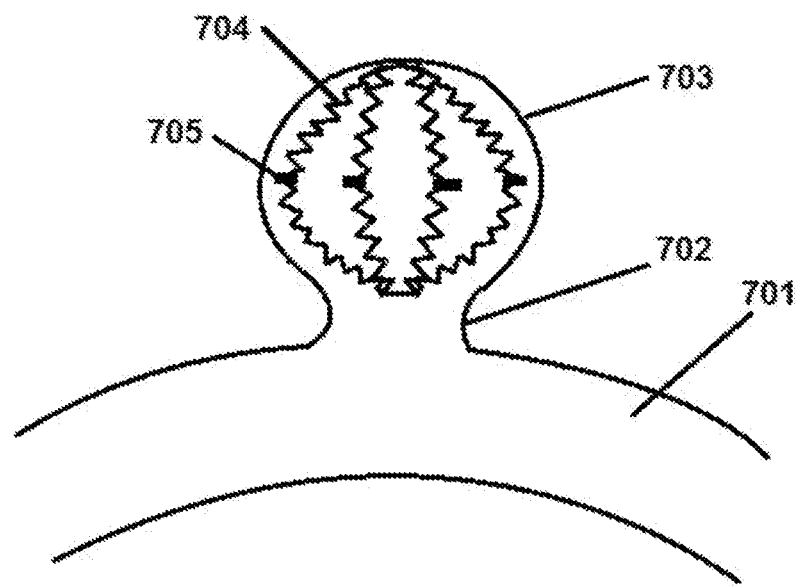
FIG. 7 is an exemplary usage of the device, where multiple devices are implanted in an aneurysm, each one forming a rib of a hollow ribbed ball-shaped structure.

It is possible for multiple devices to be implanted in an aneurysm at various positions. Following from the hollow ribbed ball-shaped structure from FIG. 6, it is possible to make the ribs from expandable coils of devices. FIG. 7 shows an exemplary device, where multiple devices are implanted in an aneurysm 703. Each coil 704 is positioned in a ball-shaped structure so that the coil rests along the aneurysm wall, with each coil comprising a capacitor 705 as well. An aneurysm may not distend uniformly due to increased pressure, but instead may distend more at some locations on the aneurysm wall than others. By including multiple devices in the aneurysm, it may be possible for one coil to show more significant inductance change during a cardiac cycle than others. The coils could be implanted using a catheter through the artery 701 and aneurysm neck 702.

If a coiling procedure is used to lessen the chance of aneurysm rupture, it may happen that the coiling is not effective at preventing blood flow into the aneurysm. In this case, the wall near the neck of the aneurysm may expand, whereas the region of the aneurysm farthest from the artery may not expand at all. By properly positioning coils in the aneurysm near and around the neck, blood flow can be detected by measuring the distension of the aneurysm wall near the neck.

The capacitor may be a fixed value or it may be variable. If the capacitor is variable, it can change based on a sensed characteristic of the environment. For example, the capacitor could be variable based on pressure or temperature. The variable capacitance also affects the inductance of the tank circuit, and can be sensed by evaluating the impedance of an interrogator coil. By including a measurement of pressure or temperature, additional information may be found about the vessel. For example, if a positive change in pressure results in increased capacitance, and distension of the vessel also results in increased inductance of the coil, the two would combine to make the change in resonant frequency of the tank circuit more significant.

Figure 8:
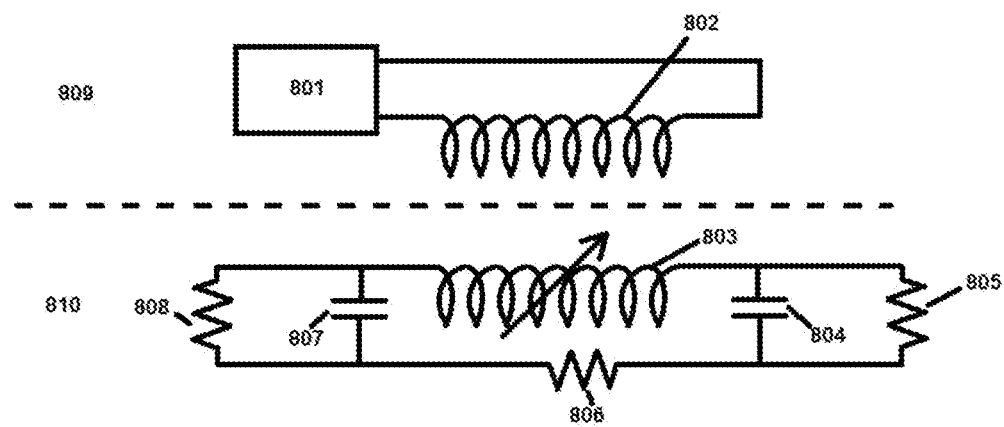
FIG. 8 is a simplified electrical model of a device that comprises two electrodes instead of a capacitor, where the capacitance is created by the electrode-tissue interface.

It is possible for the device to comprise two electrodes in series with the coil. The electrodes could take the place of a capacitor, or the electrodes could be in addition to a capacitor. FIG. 8 shows a simplified electrical model of a device that comprises the two electrodes instead of a capacitor. One electrode-material interface is represented by a parallel capacitance 804 and resistance 805. The other electrode-material interface is also represented by a parallel capacitance 807 and resistance 808. The resistance 806 models the series resistance of each electrode-tissue interface, as well as the resistance of the material between the two electrodes. The variable inductance is based on the area inside the coil. The resistance and capacitance of the electrode-tissue interface can vary based upon the characteristics of the material touching each electrode. The change in capacitance will result in a shift in the resonant frequency of the device, which can be detected by the external module 809 through a spectrum analyzer 801 or other impedance measuring device known to those skilled in the art, using an interrogator coil 802. The spectrum analyzer may also include a signal generator. Change in the electrode-material interface capacitance 804, 807, resistance 805, 808 or the series impedance 806 of the interfaces and material will affect the Q-factor of the device, which can also be detected. This allows the user to detect a change in the material around the electrodes and in the vessel. This may be useful in detection of occlusions in the vessel. If the device is incorporated into a stent, it can detect in-stent restenosis.

Figure 9:
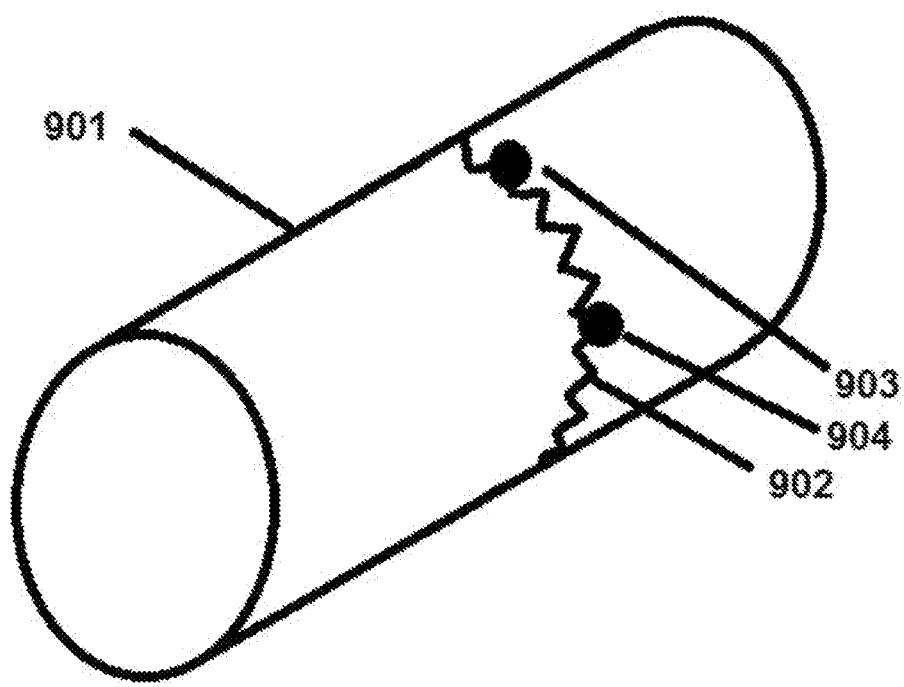
FIG. 9 is an exemplary device where two electrodes replace the capacitor, and the capacitance is a result of the electrode-tissue interface.

FIG. 9 shows an exemplary device wherein two electrodes replace the capacitor. The coil 902 is positioned along the wall of the vessel 901, and two electrodes 903,904 in series with the coil are positioned so that they are situated within the material where a change in impedance may be measured. For example, if the vessel is an artery, the coil provides a measure of the compliance of the vessel walls by the shift in resonant frequency of the device during each cardiac cycle. The capacitance of the electrode-tissue interface will change slowly over time and will be relatively stable over a cardiac cycle. Therefore, the change in the average resonant frequency over days or weeks will track the characteristics of the material surrounding the electrodes, whereas the change in resonant frequency over a single cardiac cycle will track vessel compliance, and therefore pressure.

Zhu S., et al., "Ultrastretchable Fibers with Metallic Conductivity Using a Liquid Metal Alloy Core", 2013, Advanced Functional Materials, DOI: 10.1002/adfm.201202405, 1-7.

What is claimed is:

1. A device for measuring the compliance of an aneurysm, comprising:
   a hollow ribbed structure having a compressed delivery configuration for placement within a catheter and an expanded ball-shaped deployed configuration configured to be implanted into the aneurysm;
   a coil attached to and encircling the hollow rib structure, the coil having a number of turns and being configured to be positioned along a portion of the aneurysm when the hollow ribbed structure is in the expanded ball-shaped deployed configuration, and;
   a capacitor connected in series with the coil forming a tank circuit,
   wherein the coil is configured to expand or contract in response to the aneurysm expanding or contracting thereby causing a change in a resonant frequency of the tank circuit based on an area inside the coil that provides a measure of the compliance of the aneurysm.

2. The device of claim 1, wherein the coil is configured to encircle an interior of the aneurysm.

3. The device of claim 1, wherein the capacitor has a variable capacitance based on a characteristic of an environment around the capacitor.

4. The device of claim 3, wherein the variable capacitance is based on pressure.

5. The device of claim 3, wherein the capacitor comprises two electrodes exposed to a material inside the aneurysm, wherein the capacitance is a result of an electrode-material interface capacitance of each electrode.

6. The device of claim 1, wherein the hollow ribbed structure is configured to substantially fill a space within the aneurysm in the expanded ball-shaped configuration.

7. The device of claim 1, wherein the coil is connected to the hollow ribbed structure with a connector configured to allow the coil to expand or contract without the hollow ribbed structure needing to change shape.

8. The device of claim 1, wherein the hollow ribbed structure is configured to be compressed so as to fit inside the catheter in the compressed delivery configuration for delivery through a neck of the aneurysm.

9. A device for measuring the compliance of an aneurysm, comprising:
- a hollow ribbed structure having a compressed delivery configuration for placement within a catheter and an expanded ball-shaped deployed configuration configured to be implanted into the aneurysm, the hollow ribbed structure comprising a plurality of ribs, each rib comprising a coil having a number of turns and being configured to be positioned along an interior portion of the aneurysm when the hollow ribbed structure is in the expanded ball-shaped deployed configuration, and;
- a plurality of capacitors, wherein one of the plurality of capacitors is connected in series with a respective one of the plurality of ribs forming a plurality of tank circuits,
- wherein the plurality of coils are configured to expand or contract in response to the aneurysm expanding or contracting thereby causing a change in a resonant frequency of each of the plurality of tank circuits based on an area inside each of the plurality of coils to provide a plurality of measures of the compliance of the aneurysm.

10. The device of claim 9, wherein each capacitor has a variable capacitance based on a characteristic of an environment around the capacitor.

11. The device of claim 10, wherein the variable capacitance is based on pressure.

12. The device of claim 10, wherein each capacitor is created using two electrodes exposed to a material inside the aneurysm, wherein the capacitance is a result of an electrode-material interface capacitance of each electrode.

13. The device of claim 9, wherein the hollow ribbed structure is configured to substantially fill a space within the aneurysm in the expanded ball-shaped configuration.

14. The device of claim 9, wherein the hollow ribbed structure is configured to be compressed so as to fit inside the catheter in the compressed delivery configuration for delivery through a neck of the aneurysm.

15. A device for measuring the compliance of a vessel having a wall, comprising:
- a stent configured to be placed within a portion of the vessel;
- a first coil disposed on the stent and having a first number of turns, and a first capacitor connected in series with the first coil to form a first tank circuit, wherein the first coil is configured to expand or contract in response to expansion or contraction of the vessel causing a change in an area inside the first coil;
- a second coil disposed on the stent and having a second number of turns different than the first number of turns of the first coil, and a second capacitor connected in series with the second coil to form a second tank circuit, wherein the second coil is configured to expand or contract in response to expansion or contraction of the vessel causing a change in an area inside the first coil; and
- an external system comprising an interrogation coil, the external system being configured to differentiate between the first coil and the second coil and detect a shift in a resonant frequency from each of the first tank circuit and second tank circuit to measure a difference in pressure between the first coil and the second coil in the vessel.

* * * * *